United States Patent [19]
Jackson

[11] Patent Number: 6,136,027
[45] Date of Patent: Oct. 24, 2000

[54] CUSTOM PROSTHETIC DEVICES AND METHODS OF FABRICATING THEM USING VISIBLE REVERSE IMAGING

[75] Inventor: D. K. Jackson, Laguna Beach, Calif.

[73] Assignee: Otto Bock U.S., Inc., Plymouth, Minn.

[21] Appl. No.: 08/955,535

[22] Filed: Oct. 22, 1997

[51] Int. Cl.⁷ ..................................................... A61F 2/52
[52] U.S. Cl. .......................... 623/7; 623/901; 264/222; 264/DIG. 30
[58] Field of Search .................... 623/7, 8, 901; 264/222, 223, DIG. 30; 450/57

[56] References Cited

U.S. PATENT DOCUMENTS

| | | | |
|---|---|---|---|
| 4,086,666 | 5/1978 | Vaskys et al. | 623/7 |
| 4,401,492 | 8/1983 | Pfrommer | 623/7 |
| 4,426,742 | 1/1984 | Prahl | 623/7 |
| 4,575,805 | 3/1986 | Moermann et al. | 364/474 |
| 4,600,551 | 7/1986 | Erb | 264/222 |
| 4,735,754 | 4/1988 | Buckner | 623/27 |
| 4,821,200 | 4/1989 | Oberg | 364/474.24 |
| 5,376,323 | 12/1994 | Eaton | 264/222 |
| 5,432,703 | 7/1995 | Clynch et al. | 364/474.05 |
| 5,527,359 | 6/1996 | Nakamura et al. | 623/7 |
| 5,603,791 | 2/1997 | Weber-Unger et al. | 623/7 |
| 5,798,062 | 8/1998 | Thielbar | 623/7 |
| 5,824,075 | 10/1998 | Thielbar | 623/7 |

*Primary Examiner*—Mickey Yu
*Assistant Examiner*—Tram A. Nguyen

[57] ABSTRACT

An external custom prosthetic device is created and positioned upon a patient such that an area to be covered is matingly engaged with a product that is a simulacrum of the part desired to be replaced due to reversed imaging, by laser photography or laser mapping. A method for creating a silicone based prosthetic, process for generating same with or without an air pocket disposed therein, and products by these processes are likewise taught.

22 Claims, 6 Drawing Sheets

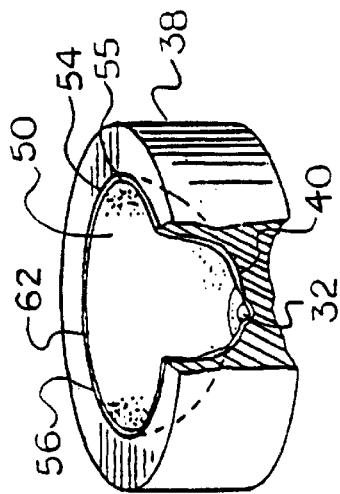
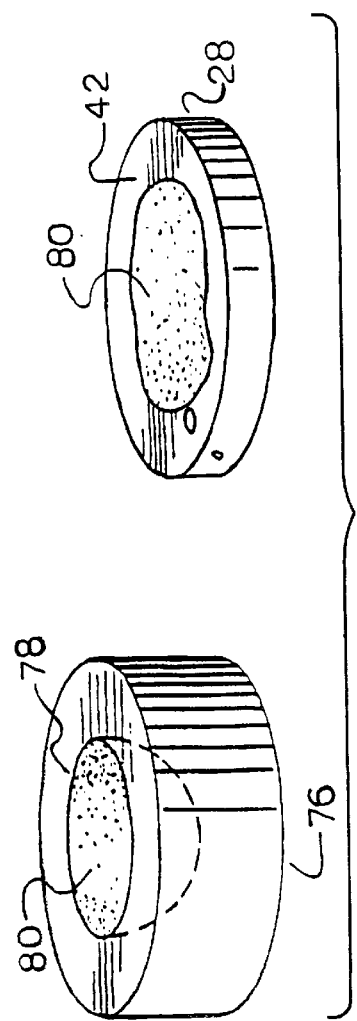
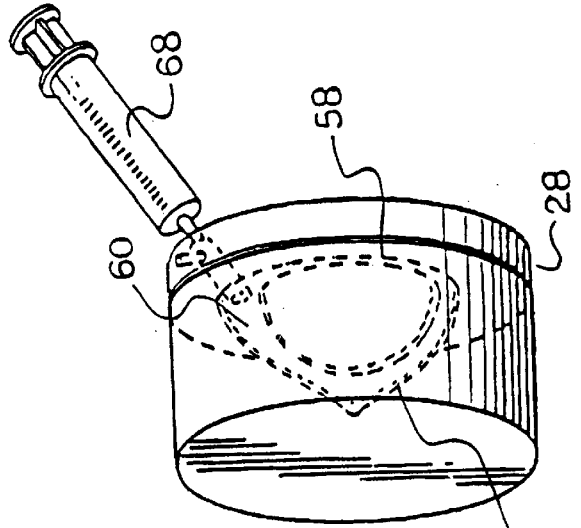
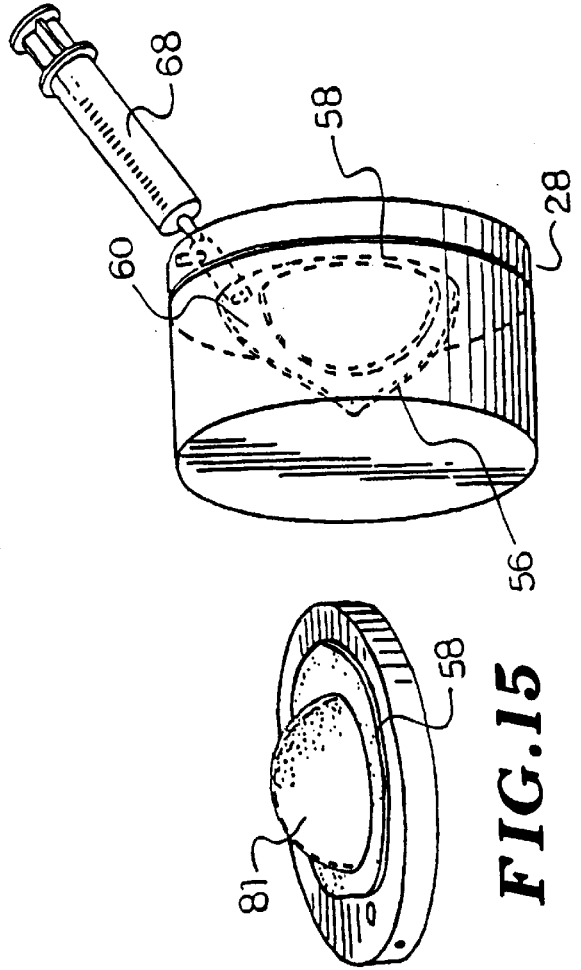

CUSTOM PROSTHETIC DEVICES AND METHODS OF FABRICATING THEM USING VISIBLE REVERSE IMAGING

BACKGROUND OF THE INVENTION

1. Field of Invention

The present invention relates to prostheses, and in particular to processes for forming and positioning customized external prostheses. Specifically, a method of forming an external custom breast prosthesis is illustrative of the teachings of the present invention, such as may be employed to replace a missing breast after surgical removal, usually performed as a treatment for cancer and commonly referred to as a mastectomy.

2. Description of the Prior Art

Over the years more patients have been using prosthetic devices, and in particular, prosthetic breasts after mastectomy operations. However, prior prosthetic breasts have not sufficiently created a method of forming a custom artificial breast that answers many of the problems associated with mastectomies. For example, the prosthetic breast may not have a realistic look, feel or shape, and may not have a proper color or simulated skin texture, particularly when only one of the two natural breasts has been removed.

Most prior known methods of forming prosthetic breasts have lacked the capability to more closely match the appearance and shape of the remaining natural breast.

Examples of the state of the prior art are found in U.S. Pat. No. 2,580,264 issued to M. A. Wright, et al.; U.S. Pat. No. 4,086,666 issued to Petras Vaskys, et al.; U.S. Pat. No. 4,401,492 issued to A. M. Pfrommer; U.S. Pat. No. 4,600,551 issued to R. A. Erb and U.S. Pat. No. 5,527,359 issued to T. Nakamura et al.

SUMMARY OF THE INVENTION

The present invention has for an important object the provision to create a custom made breast prosthesis that overcomes the outstanding problems that occur in the manufacturing process.

Another object of the present invention is to provide a prosthetic breast that closely matches a breast that has been removed as regards to shape, texture and color of the remaining natural breast of the subject, so that the prosthetic breast more perfectly simulates the removed natural breast and is a true opposite of the remaining natural breast.

A further object of the present invention is to provide a new and unique method of forming a prosthetic breast that includes the use of molding clay and employs a reverse mirror photographic technique of the remaining natural breast, whereby the molding clay can be duplicated in reverse to that of the remaining natural breast, as will hereinafter be disclosed.

Still another object of the present invention is to provide a breast prosthesis that is lightweight and comfortable to wear with most suitably formed brassiere structures.

Yet another object of the present innovation is to provide a breast that includes a nipple and the areola about the nipple of the breast that has a natural look corresponding to the nipple and areola of the natural breast.

The characteristics and advantages of the invention are further sufficiently referred to in connection with the accompanying drawings, which represent several embodiments. After considering these examples, skilled persons will understand that variations may be made, and structures, arrangements or modes of operation employed, without departing front the principles disclosed, or the scope of the invention as claimed.

BRIEF DESCRIPTION OF THE DRAWINGS

Novel features and advantages of the present invention in addition to those mentioned above will become apparent to those skilled in the art from reading the following detailed description in conjunction with the accompanying drawings wherein:

FIG. 13 is a pictorial view of the negative air pocket mold and the back mold with silicone applied to the mold, the gel being indicated by stippling;

FIG. 14 is a pictorial view of the negative breast mold broken away to show the silicone breast wall structure being formed therein;

FIG. 15 is a pictorial view of the air pocket mold being used to create a silicone air pocket wall structure and an integral silicone back wall for both the air pocket and the silicone breast wall structure;

FIG. 16 is a pictorial view of the negative breast mold and the back mold secured together;

DETAILED DESCRIPTION OF THE PREFERRED EMBODIMENTS

Figure 1:
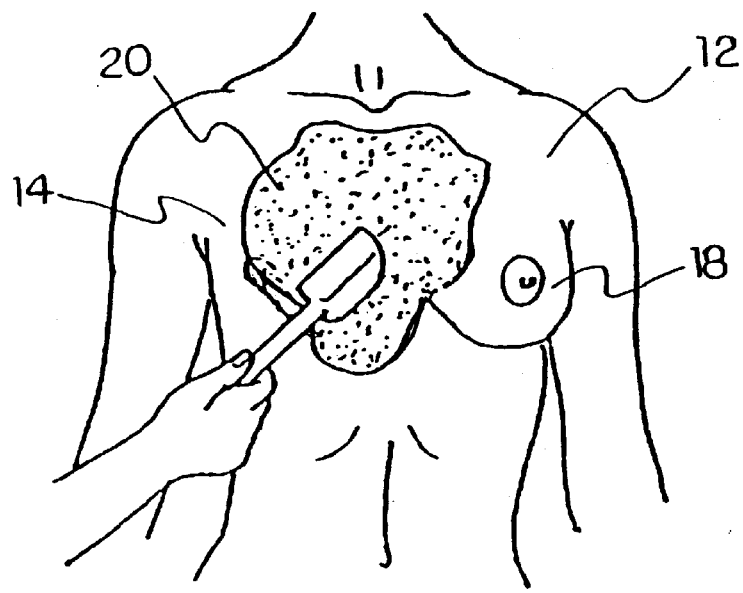
FIG. 1 is a front elevational view showing a woman patient with her breast removed as by a mastectomy over which is being applied a coating of molding material that will define a negative impression.
Figure 2:
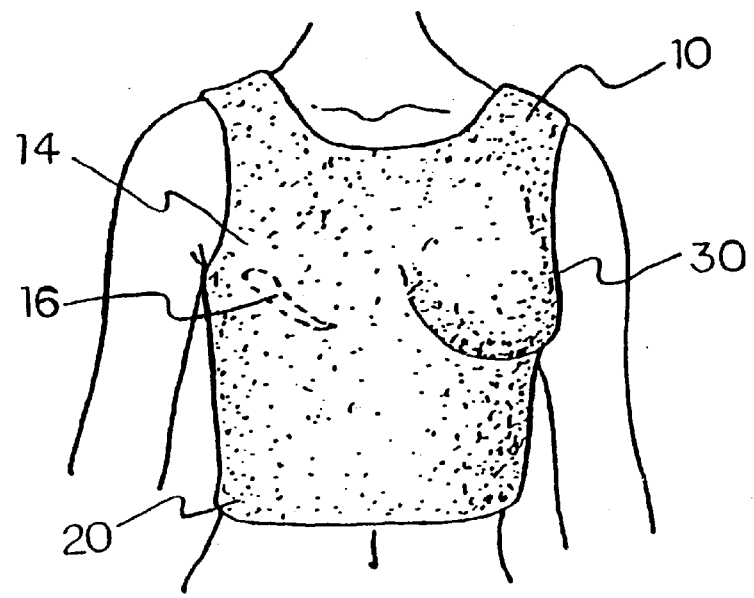
FIG. 2 is a front elevational view showing the finished negative casting of the upper torso which includes a portion of the sides and shoulders of the patient and an impression of her natural breast.
Figure 5:
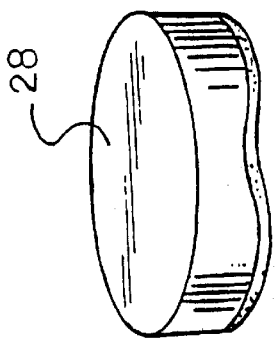
FIG. 5 shows a back mold made of the scar area from the positive cast.

The present inventor has discovered at least three ways to overcome the drawbacks known in the art. Both the process and method disclosed herein may be used with the laser enhanced technology depicted in FIG. 18, for precisely mapping and replicating local surface topography of a patient. In the following discussion, the steps and structures defining at least two of the three distinct embodiments are similar to the extent of forming a negative cast or mold, shown generally at 10 throughout. Referring now to FIG. 1 and FIG. 2, a patient's or subject's upper torso is shown generally designated at 12, particularly the area 14 of a missing breast, including a scarred portion 16 along with a natural breast 18. In the illustration depicted, a right breast is shown as being removed and a left breast defines the remaining, natural breast 18. No limitations in size or shape are claimed.

A negative cast or mold 10 is made either by covering an entire chest area, including the depicted zone underneath the arms and down to the waist with a suitable spreading paste material (such as gypsum plaster) indicated by stippling 20, as is known in cast molding, along with at least one layer of wet precut bandages or gauze material (not shown); or by way of a laser defined and computer generated set of data points performing an analogous function. The latter is depicted schematically at FIG. 18. For all intents and purposes, this variation on the steps described in detail hereafter will become known to those skilled in light of the claims hereafter.

A second casting or mold is a positive impression of the negative mold 10, whereby a positive mold is made of a patient's torso, shown generally at 22. Mold 22 is made from a suitable paste with a first coat being thinly spread on an inner surface of the negative mold 10. This is followed by a thicker coat of plaster that has at least a ¾ inch thickness over the entire negative impression. At the proper time the positive mold 22 is removed from the negative mold 10.

Since, as illustrated, the right breast has been removed a prosthetic replacement is formed. This is accomplished by adding at least two novel steps to the process. When the positive mold is finished a reverse photograph is taken of the patient's natural existing breast while the patient is standing in front of a mirror.

Thus, the left natural breast when shown in reverse in the photo looks like the missing right breast. This allows the missing right breast to be perfectly simulated, whereby a prosthetic breast can be sculptured and formed from a mound of molding clay 24 so as to have the identical reverse configuration of the natural left breast 18. If the patient chooses, the clay breast can be sculptured to replicate a more pendulous breast or one that is shaped to be worn inside a typical brassiere.

Figure 7:
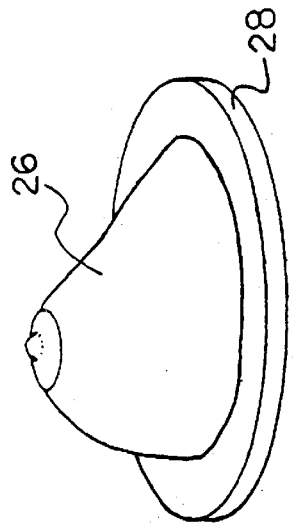
FIG. 7 is a pictorial view of the finished clay breast model mounted to the back mold.
Figure 4:
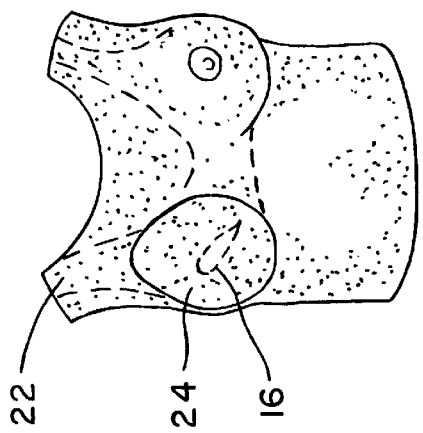
FIG. 4 is a view similar to that of FIG. 3, wherein the scar area is shown covered with a deposit of modeling clay.
Figure 3:
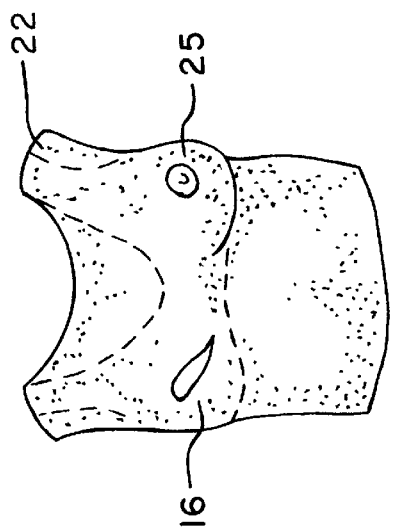
FIG. 3 is an elevational view showing a positive mold made from the negative mold showing the natural breast and scar left by the mastectomy procedure.
Figure 6:
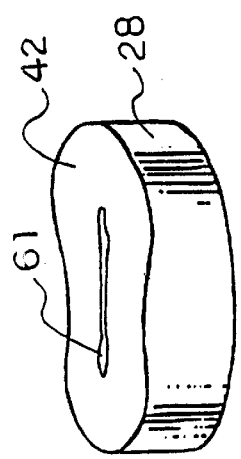
FIG. 6 shows the back mold including a negative impression of the scar area.

Accordingly, the mound of moldable clay 24 is placed over scar tissue area 16 of the incision as provided by positive cast or mold 22 illustrated in FIG. 4. The clay is then sculptured with respect to what is shown in the photograph and the cast of the natural left breast 25 which is now juxtaposed to clay mold. The clay version of the right breast now simulates the approximate right side configuration of a prosthetic breast, indicated generally at 26. Once the molded clay breast 26 is formed it is removed from the positive cast and is then placed on a small back mold 28, as illustrated in FIG. 7. The small back mold 28 is made by covering the scar area 16 on the negative cast 20 with gypsum plaster approximately ½ inch thick. Once dried in an oven at temperatures of between 80 to 150 degrees, the back mold 28 is sprayed with a mold release over the scar impression, as seen in FIG. 6.

Figure 8A:
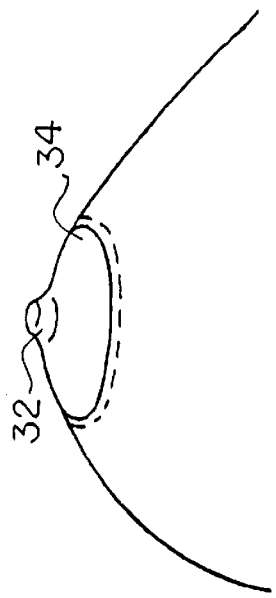
FIGS. 8 and 8A are pictorial views of a nipple and areola mounted to the sculptured clay breast model.

A silicone replica of the patient's nipple and areola is reproduced from the negative cast 20, indicated at dotted lines 30 in FIG. 2. The silicone of the nipple and the areola is colored to match the patient's nipple color. The silicone nipple 32 and the integrally formed areola 34 is taken from negative cast 20 and pushed into the clay of breast 26, as indicated in FIG. 8, at which time the annular edge of the areola 34 is overlapped with moist clay as shown in FIG. 8A, by a suitable means such as one's finger.

Figure 8C:
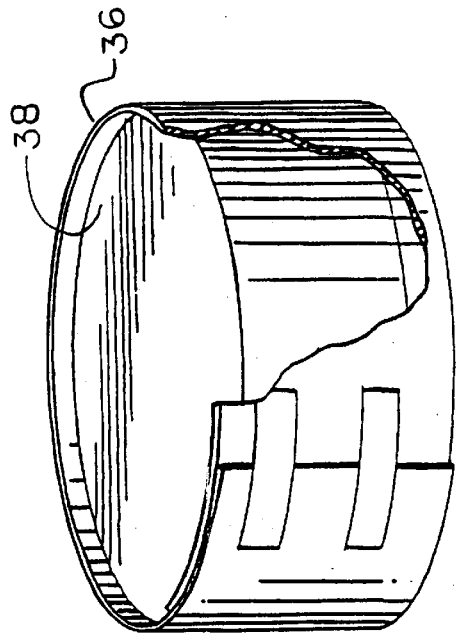
FIGS. 8B and 8C are pictorial views in sequence showing the process of making a negative breast mold formed from the finished clay breast model.
Figure 8:
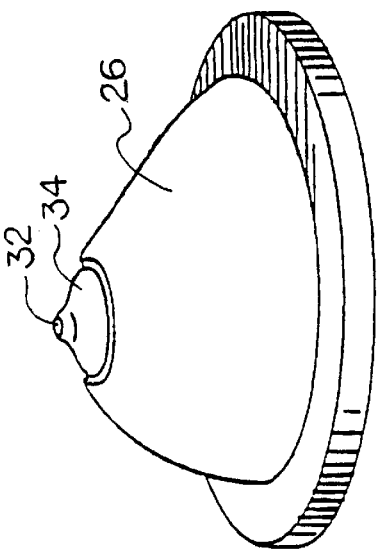
Figure 8B:
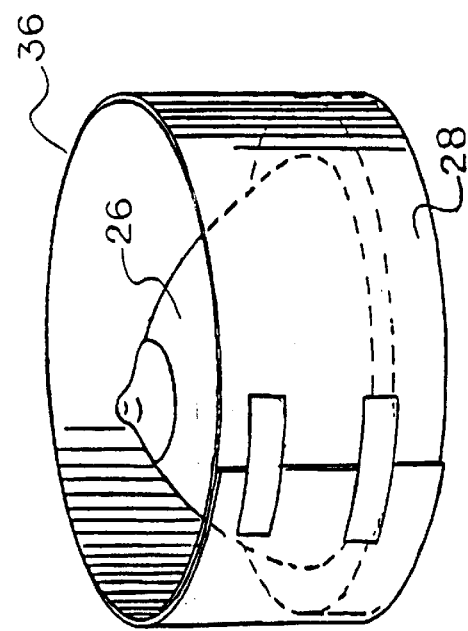
Figure 11:
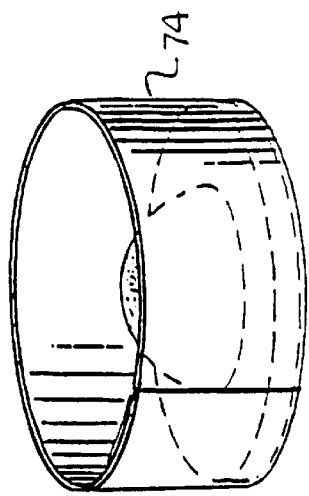
FIG. 11 is a pictorial view of the finished clay air pocket mold being prepared to form a negative air pocket silicone wall structure.

When nipple 32 is secured to the clay breast 26 an annular wall 36 is positioned around back mold 28 and the clay mold 26, as illustrated in FIGS. 8B and 8C. The next step is to cast a negative breast mold 38 of the clay breast together with the mounted nipple 32 by pouring plaster over the clay breast inside wall 36. The new negative breast mold 38 when fully cured at a suitable temperature is then removed from the clay breast. At this time both the inner casting surface 40 of the breast mold 38 and the scar surface 42 of the small back mold 28 are sanded smooth. The small back mold 28 is then drilled to define an inlet passage 44 that extends from the back surface 46 to the surface 42. A second passage is drilled into the annular edge 47 of back mold 28 to define an air passage 48 that communicates with inlet passage 44 which allows a gel to be injected through the wall of mold 28. The gel injection step will be described in more detail hereinafter. For ease of explanation, the nipple 32 will include the integrally formed areola 34.

Referring to FIG. 14, the inner surface is first sprayed with a release agent over the casting surface 40 that defines a cavity 50 of mold 38, after which the color matched nipple 32 is positioned at the bottom of cavity 50. A silicone layer 54, colored to match the skin tone of the patient, is used to coat the skin-like wall structure 55 at a thickness of approximately ¹⁄₁₆". The silicone skin and the nipple are then allowed to cure together, thereby forming a silicone breast body 56 of the simulated breast.

Figure 17:
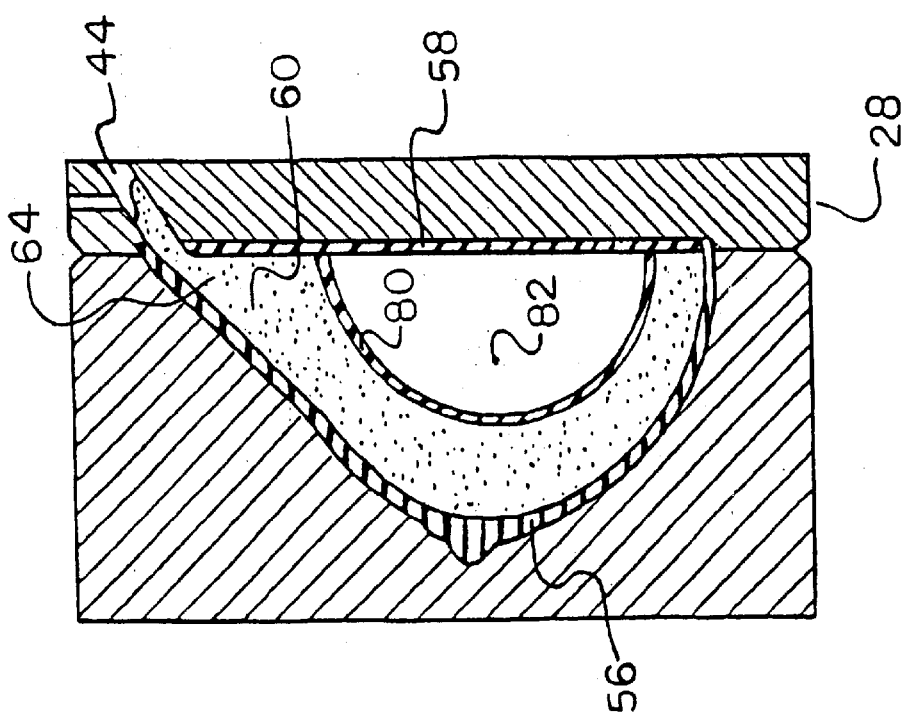
FIG. 17 is a mid-sagittal view of a completed external custom prosthetic device according to the instant teachings which may be removedly affixed to a user according to the novel method of positioning, on the body of a patient, an external custom breast prosthesis as taught herein.

Once breast body 56 is formed, a silicone rear breast wall structure 58 is then formed. Body 56 and structure 58 are singularly or integrally cured together to form a sealed compartment or chamber 60. Accordingly, rear wall structure 58 comprises a silicone coating, as illustrated by a phantom line in FIG. 16, having a suitable thickness that covers the scar imprint 61 formed on molded surface 42 of back mold 28. The silicone rear wall 58 must include a large enough area so as to cover opening 62 defined by breast body 56 of the simulated breast (see FIG. 14) and also cover inlet passage 44. After the breast mold 38 is coated to define the silicone breast body 56, it is secured together with the silicone rear wall coating 58 that covers back mold 28, as illustrated in FIG. 16. The two silicone coatings are then cured together in a heat chamber for a suitable time period, whereby the sealed compartment 60 is formed between the silicone breast body 56 and the silicone rear wall 58, as indicated in FIG. 17.

The next steps include filling chamber 60 with a suitable gel-type silicone material 64 by injecting the get 64 through a hole in rear wall 58 by means of a suitable injector 68. The hole is then covered and sealed either before or after the two coupled molds are separated from each other.

The second embodiment of the invention includes all of the steps of the first embodiment of the invention including all the steps as described relating to FIGS. 1 through 14.

Accordingly, after the step wherein the inner surface has been sanded smooth, mold 38 is then sprayed with a release agent over inner casting surface 40 that defines a cavity 50, with the color matched nipple 32 positioned at the bottom of cavity 50. A silicone layer, 54, colored to match the skin tone of the patient, is then applied to coat the skin-like wall 55 structure at a thickness of approximately 1/16". The silicone skin and the nipple are then allowed to cure together, thereby forming a silicone breast body 56 of the simulated breast. Once the breast body 56 is formed, the silicone rear breast wall structure 58 is also formed as previously described.

Figure 10:
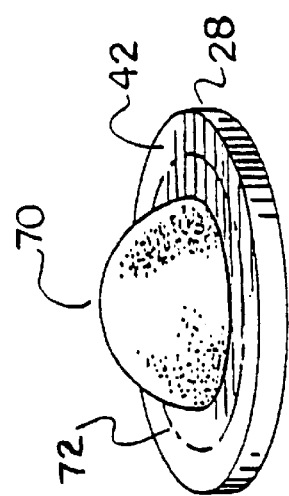
FIG. 10 is an alternative clay mold formed from the original finished clay mold so as to define a clay air pocket mold used in an alternative breast forming process to form a silicone air pocket.
Figure 9:
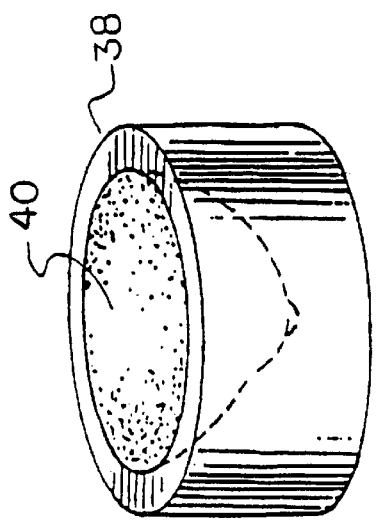
FIG. 9 is a pictorial view of the finished negative breast mold in which an outer finished wall silicone breast structure is formed.
Figure 12:
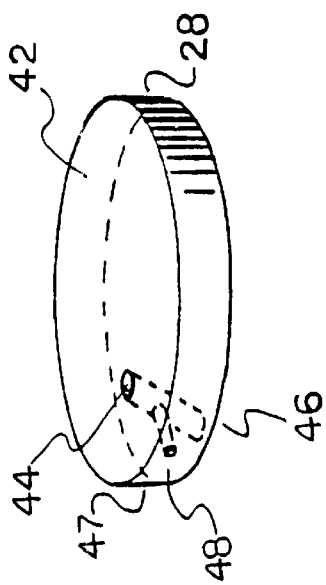
FIG. 12 is a perspective view of the back mold having a pair of intersecting passages used to inject a silicone gel.

After the silicone breast body 56 and the rear breast wall 58 are formed the next step for creating the second embodiment includes removing the silicone nipple 32 from the formed molded clay breast 26 while it is still secured to the back mold 28, as illustrated in FIGS. 8A and 8B. Using a sculpting raking tool (not shown), at least ¾" of clay is removed from the clay breast 26 to form a hemispherical clay mold 70, as shown in FIG. 10, defining an air pocket clay mold. The phantom lines 72 indicate the outline or size of the original clay breast 26. The surface 42 of the back mold 28 and the hemispherical clay mold 70 are enclosed in an annular wall 74 in which is poured molding material such as gypsum plaster which is cured to form a hemispherical recessed mold 76 and the inner surface 78 of the mold is sanded. A coat of silicone 80 is spread over the inner surface 78 to provide a silicone inner wall 81, and over back mold 28 to provide rear silicone breast wall member 58. FIG. 17 illustrates a resultant position following utilization of the method for positioning according to the teachings of the present invention, and further shows a hemispherical air pocket 82 formed by wall member 58 and inner wall 81.

Figure 18:
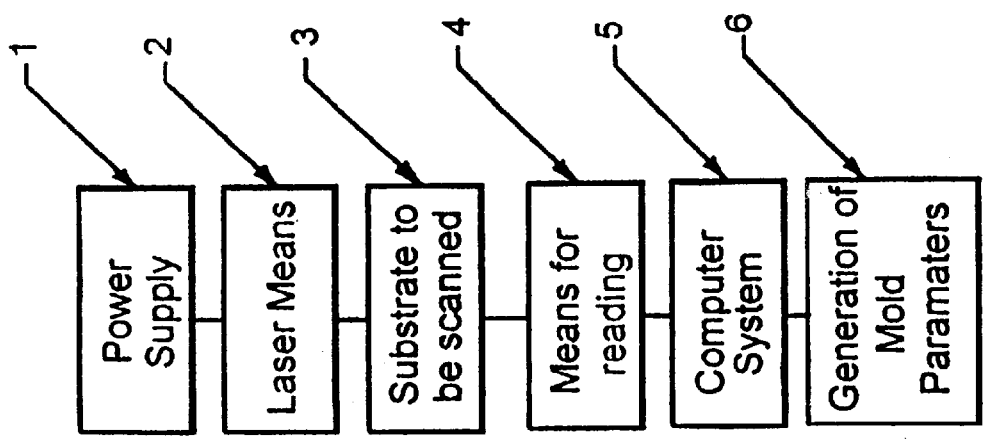
FIG. 18 depicts schematically the steps according to an alternate embodiment of the novel enhanced means for generating and positioning a prosthetic apparatus according to the instant teachings.

Referring now to FIG. 18, a schematic illustrates an alternate preferred embodiment according to the instant teachings. The principles and process steps of both embodiments discussed in detail thus far are each supplemented by the use of an intermediate means for generating and positioning a prosthetic apparatus as illustrated and explained by this figure.

Namely, it is known to user power supplies (not claimed) for light amplification for the stimulated emission of radiation (LASER) at a level wherein the laser beam frequency does not excite either vibrational or rotational states of the irradiated species—but rather may be used as a means for generating an extremely precise set of data points concerning local topographic features. The teachings of the present invention derive a portion of their novelty from the mating engagement of the custom prosthetic with the substrate area on a patient. This feature is based both upon spatial, geometrical and gross surface features of the teachings of the present invention.

Not unlike classical enzymatic "lock and key" theory, the teachings of the present invention provide a means for affixingly bracing a custom fitted prosthesis upon a target area in a user. By calibrating known means for measuring and translating such data into arrays of computer readable characters, the teachings of the present invention allow a patient to be more precisely fitted with a custom sized prosthetic apparatus.

Referring now to FIG. 18, a flow-chart shows how a laser generated set of precise data points can result in an alternate preferred embodiment of the present invention. Quite unexpectedly, the compound used within the context of the present invention has been developed having an africtional hand, or a strong resistance to sliding along the surface of a substrate. In combination with the reverse photographic image of the instant teachings, this has resulted in a prosthetic that 'goes both ways' or fits both into the area of the body to be treated and into the visual and tactile perception of one observing same appended to a patient. Still referring to FIG. 18, using power supply 1 (not claimed) and known laser means 2 an intermediate step which complements the above described processes may be undertaken. For example, the mastectomy scar may be the substrate to be scanned 3 by laser probe scanning and CAD/CAM (Computer Aided Design/Computer AIded Manufacturing) procedures for more accurately generating a three-dimensional design, which is used to generate a plurality of relevant data points and information regarding the local topography of the information mapping, for example, scar area 4 may be conventional or to be developed software or the like mechanisms for arraying and manipulating data streams. Integration of same with computer system 5 enables a patient's information to be further processed and to generate, for example, computer aided design or the like three dimensional modeling schemes to be employed as for the generation of mold parameters 6, with the rest of the process steps being identical to the described above and claimed below. Likewise, using digital cameras and modems, in addition to multiple imaging cameras having spatial and local geographic positioning indices will continue to make the mapping of scar areas to be treated more and more precise. It has been shown that the fit between the products produced under the methods and processes of the present invention and the scar areas of users provides heretofor uncontemplated advantage. Better fit removes chafing, discomfort and the general lack of confidence found with any known external breast prosthetic devices. This principle applies equally to other body areas, but has been well demonstrated according to the instant teachings.

Accordingly, one of the few improvements assailable within the context of the instant teachings was a "better fit" with, for example, the scar area of a mastectomy. By using laser imaging, the present inventor has taken a known means for laser beam generation, used it upon a substrate to be scanned, employed means for reading, and run same through a computer system having software effective for generating molding parameters to create an even closer match with the substrate area targeted.

What is claimed:

1. A process for fabricating a custom prosthesis for use in lieu of one of a pair of natural body members of a subject, including:

forming a negative cast mold of a portion of a body of a subject including at least an attachment site from which one of a pair of natural body members has been removed, and against which a prosthesis is to be attached in lieu of a removed one of the pair of natural body members;

forming a positive impression of said negative cast mold, said positive impression including a replication of the attachment site;

coating the positive impression with a curable material to form a first prosthesis wall;

generating a visible reverse image of another, remaining one of the pair of natural body members;

using the visible reverse image to form a positive body member mold simulating said visible reverse image;

forming a negative cast mold of the positive body member mold to provide a negative body member mold;

coating the negative body member mold with a curable material to form a second prosthesis wall;

juxtaposing the first prosthesis wall and the second prosthesis wall such that the prosthesis walls contact one another and cooperate to enclose a chamber; and bonding the prosthesis walls to one another while they are so juxtaposed, to form an external prosthetic enclosure.

2. The process of claim 1 further including:

after bonding said walls, injecting a filler medium into the chamber.

3. The process of claim 2 wherein:

the filler medium comprises a silicone gel.

4. The process of claim 1 wherein:

generating the visible reverse image comprises using a mirror to take a reverse image photograph of one of: the remaining natural body member, and a replica of the remaining natural body member.

5. The process of claim 4 wherein:

the replica of the remaining natural body member comprises a portion of said positive impression.

6. The process of claim 1 wherein:

generating the visible reverse image comprises measuring one of: the remaining natural body member, and a replica of the remaining natural body member.

7. The process of claim 6 wherein:

said measuring is performed using a laser.

8. The process of claim 1 wherein:

forming the positive body member mold comprises sculpting clay.

9. The process of claim 8 wherein:

forming the negative body member mold comprises juxtaposing the positive body member mold and the positive impression against one another with a rearward portion of the positive body member mold against said replication of the attachment site;

surrounding the juxtaposed positive body member mold and positive impression with a containment wall; and filling the space between the juxtaposed positive mold and positive impression and containment wall with a casting material.

10. The process of claim 1 wherein:

bonding the first and second walls comprises curing the first and second walls simultaneously while they are so juxtaposed.

11. The process of claim 1 wherein:

the bonding of the first and second walls seals the chamber.

12. A custom prosthesis formed according to the process of claim 1.

13. A custom prosthesis formed according to the process of claim 2.

14. The process of claim 1 further including:

fabricating an inner wall of a curable material;

with the first and second walls so juxtaposed, further juxtaposing the inner wall against the first wall and in the chamber; and bonding the inner wall to the first wall to form an air pocket within the chamber.

15. The process of claim 14 wherein:

bonding of the inner wall and first wall seals the air pocket.

16. The process of claim 15 further including:

injecting a filler medium into the chamber and outside of the air pocket.

17. A custom prosthesis formed according to the process of claim 14.

18. A custom prosthesis formed according to the process of claim 16.

19. A process for fabricating a custom prosthesis, including:

forming a negative cast mold of a portion of a body of a subject including at least a prosthesis attachment site, by covering a desired portion of the body with a first layer of a paste material wherein the desired portion includes a substantially larger area than the area to be treated, and disposing upon the paste material at least one covering layer;

forming a positive impression of said negative cast mold by applying at least a first coat of a paste material upon an inner surface of the negative cast mold, and removing the positive impression from the inner surface of the negative cast mold;

generating a visible reverse image of a desired aspect of the body to be replicated, based on parameters measured from at least one member selected from the group consisting of an existing section of the body to be replicated and a reshaped surrogate of said section;

simulating the visible reversed image to form a sculptured model that mimics the visible reversed image;

spraying the positive impression of the negative cast mold with a mold release agent, at least over a portion thereof including the attachment site;

matingly coupling a posterior surface of said sculptured model with said positive impression of the negative cast mold at the prosthesis attachment site;

producing a silicone replica of a nipple and areola, coloring said replica, and pushing the replica into said sculptured model;

after so positioning said replica, surrounding the coupled positive impression and sculptured model with a containment wall;

after said surrounding, casting a negative breast mold of the sculptured model and mounted replica by filling the space bounded by the containment wall with poured plaster;

curing and removing the negative breast mold;

sanding smooth an inner surface of the negative breast mold, and sanding smooth the positive impression of the negative cast mold at least at said attachment site;

coating the positive impression with a curable material to form a first prosthesis wall;

coating the negative breast mold with a curable material to form a second prosthesis wall;

juxtaposing the first prosthesis wall and the second prosthesis wall such that the prosthesis walls contact one another and cooperate to enclose a chamber; and bonding the prosthesis walls to one another while they are so juxtaposed, to form an external prosthetic enclosure.

20. The process of claim 19, further including:

drilling said positive impression, after said sanding, to define a first passage extending from a back surface of the positive impression to the prosthesis attachment site;

drilling a second passage into an edge of the positive impression to define an air passage that communicates with the first passage.

21. The process of claim 20 further including:

filling the chamber with a silicone gel material by injecting the gel material through the first passage;

covering and sealing the first passage; and separating the negative breast mold from the positive impression.

22. The process of claim 19 further including:

forming an inlet passage extending from an outer surface of the sculptured model to the chamber;

connecting the inlet passage with a communication passage to allow passage of a medium therethrough; and injecting said medium.

* * * * *